United States Patent [19]

Akomer

[11] Patent Number: 4,596,463
[45] Date of Patent: Jun. 24, 1986

[54] ATOMIC SPECTROSCOPY SURFACE BURNER

[76] Inventor: Errol Akomer, 2701 De Soto Dr., Miramar, Fla. 33023

[21] Appl. No.: 554,219

[22] Filed: Nov. 22, 1983

[51] Int. Cl.[4] .......................... G01J 3/30; G01N 21/72
[52] U.S. Cl. ..................................... 356/315; 356/417
[58] Field of Search .................... 356/315, 417; 431/4, 431/126; 239/568, 597

[56] References Cited

U.S. PATENT DOCUMENTS

| | | | |
|---|---|---|---|
| 3,208,333 | 9/1965 | Gibert, Jr. | 356/315 |
| 3,409,233 | 11/1968 | Kiernan | 239/568 |
| 3,434,668 | 3/1969 | Boling | 239/568 |
| 3,438,711 | 4/1969 | Hell | 356/315 |
| 3,516,771 | 6/1970 | Rendina | 356/315 |
| 3,698,643 | 10/1972 | Cummings et al. | 239/568 |
| 3,763,385 | 10/1973 | Mossotti et al. | 356/315 |
| 3,810,583 | 5/1974 | George | 239/597 |
| 3,870,234 | 3/1975 | Stupar | 356/315 |
| 4,420,255 | 12/1983 | DeWilde et al. | 356/315 |

OTHER PUBLICATIONS

"Circular Slot Burner-Droplet Generator System for High-Temperature Reaction and Vapor Transport Studies", Joshi et al., *Anal. Chem*, vol. 51, No. 11, p. 1781, Sep. 1979.

"An Improved Nitrous Oxide Burner for Atomic Absorption Spectroscopy", R. Goguel, *M.Z. Jl. Sci.*, vol. 13, No. 4, p. 603, Dec. 1970.

*Primary Examiner*—F. L. Evans
*Assistant Examiner*—Joel L. Harringa
*Attorney, Agent, or Firm*—Herbert L. Lerner; Laurence A. Greenberg

[57] ABSTRACT

An atomic spectroscopy surface burner, includes a housing having at least one channel for carrying fuel and at least one separate channel for carrying oxidant formed therein, the housing having an upper surface with two elongated slots formed therein, each of the slots being in communication with a respective one of the channels for delivering fuel and oxidant separately to the surface, and means for delivering a nebulized sample to the surface through one of the channels.

19 Claims, 7 Drawing Figures

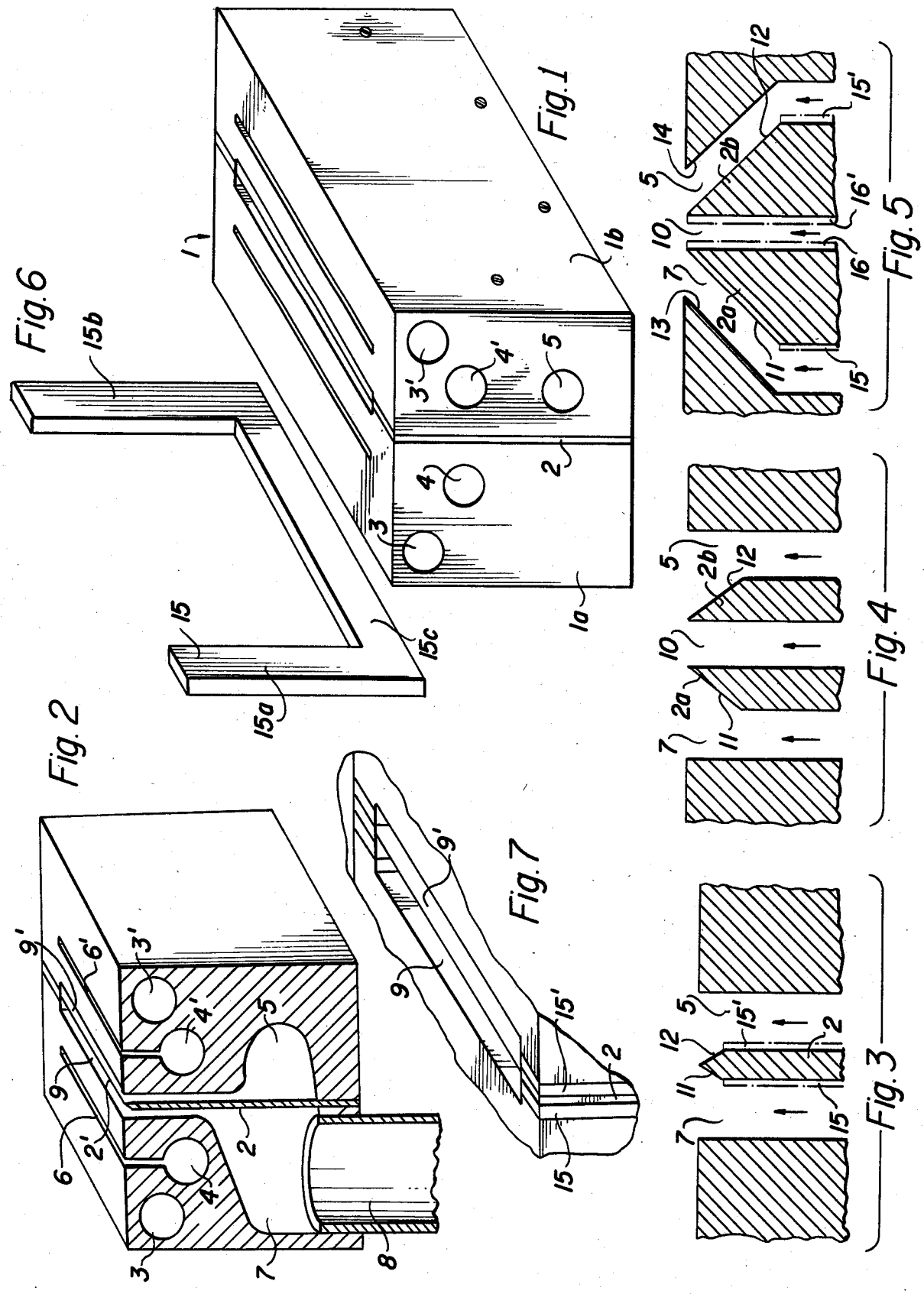

ATOMIC SPECTROSCOPY SURFACE BURNER

The invention relates to an atomic spectroscopy surface burner, to be placed between a radiation source and a monochromator for chemical analysis of a sample fed to the burner flame.

Chapter 10 of the book entitled "Instrumental Analysis", published by Allyn & Bacon, June 1979, by Gary D. Christian discusses various forms of flame spectroscopy, including atomic absorption and atomic emission spectroscopy. For atomic absorption, a burner is disposed between a radiation source and a monochromator followed by a detector, as shown on page 279 of the publication. An atomizer turns the sample into an aerosol before it reaches the burner.

Basically, two types of burners are in use, namely premix and surface burners. Both of these burners have advantages and disadvantages which are discussed on pages 270 and 271 of the publication, and the burners themselves are shown on pages 268 and 269. Premix burners are additionally the subject of U.S. Pat. Nos. 3,434,668; 3,438,711; 3,516,771; 3,698,643; and 3,870,234. U.S. Pat. No. 3,409,233 describes a surface burner which is used for scarfing, not atomic spectroscopy.

The radiation from the source can only be absorbed by neutral or un-ionized free atoms. Therefore the degree of absorption is directly related to the concentration of free atoms in the flame. Several factors related to the flame govern the concentration of free atoms. These are the temperature, and the environment of the flame, namely the concentration of sample being aspirated or reaching the flame which is the atomization efficiency, the shape of the flame, etc.

In the premix burner, the sample, oxidant and fuel are all fed to a common mixing chamber where they are intermixed upstream of the burner. The mixture is then fed to the burner and ignited along a slot. The most outstanding disadvantage of the premix burner is that only low burning-velocity flames can be used. A burning velocity which is higher than the rate of flow gases leaving the burner, will cause the flame to travel down into the burner resulting in an explosion commonly known as flashback. Because of this limitation it is somewhat difficult to use high burning-velocity gases, which includes oxygen-based flames. Accordingly, more than 90% of the sample does not reach the flame and travels back through the mixing chamber and out a waste drain. The major advantage is that the sample which does reach the flame is efficiently atomized and the slot at the top of the burner provides a long path length for the laminar flame.

In conventional surface burners, also known as turbulent or total consumption burners, a capillary tube carries the sample to a hole at the surface of the burner. The oxidant emerges to the surface at an annular opening around the capillary opening and the fuel emerges at an annular opening around the oxidant opening. This causes the sample to be drawn out and to be broken up. In the process, the sample is fragmented and nebulized into a spray, the spray is decomposed by dissolvation into a dry aerosol and the aerosol is heated to form a vapor which contains molecules, atoms and ions. The temperature and environment of the flame help to determine the proportion of molecules to ions to free atoms which can be detected.

The greatest disadvantage of surface burners is that although the entire sample is aspirated, vaporization and atomization is poor. The resulting drops are relatively large which will cause the flame temperature to fluctuate and will scatter the source radiation. This may cause false measurements to be detected. This type of burner is noisy to the detector as well as to the ear, possibly on a level similar to that of a jet engine. Another major disadvantage is that the path length is extremely short, since combustion occurs only at a point above the capillary tube.

The most important advantages of a surface burner are that there is no explosive hazard, solutions containing large solids can be aspirated and the burner is easy to clean and maintain.

It is accordingly an object of the invention to provide an atomic spectroscopy surface burner which overcomes the hereinafore-mentioned disadvantages of the heretofore-known surface burners of this general type, and to increase the flame path length while providing a laminar flame, as opposed to conventional surface burners. At the same time it is an object of the invention to include the many advantages of a long path length premix burner, and have the ability to use high burning-velocity gases.

With the foregoing and other objects in view there is provided, in accordance with the invention, an atomic spectroscopy surface burner, comprising a housing having at least one channel for carrying fuel and at least one separate channel for carrying oxidant formed therein, the housing having an upper surface with two elongated slots formed therein, each of the slots being in communication with a respective one of the channels for delivering fuel and oxidant separately to the surface, and means for delivering a nebulized sample to the surface through one of the channels.

Through the use of the burner of the invention, the advantages of premix and surface burners are combined in a single surface burner, namely:

(a) the elimination of an explosive hazard even with a high burning-velocity;
(b) the ability to change the flame environment by using different gas combinations or flow rates;
(c) the ability to easily clean and maintain the burner;
(d) the ability to separately control nebulization so that uniform droplets are introduced into the flame, reducing light scattering;
(e) the formation of a noiseless, laminar flame;
(f) the provision of a long path length;
(g) the elimination of encrustations caused by large drops;
(h) lower costs for producing the burner because it is simply constructed and lower costs for operating the burner since there is no minimum flow rate for oxygen based flames, allowing less gas to be used;
(i) the ability to use the burner for chemical analysis of virtually any sample, without the neccessity for changing burners when changing gases; and
(j) the elimination of flashback during lighting and extinguishing the flame.

In accordance with another feature of the invention, the slots are elongated in axial direction of the channels.

In accordance with a further feature of the invention, the housing has a given length in longitudinal direction of the slots, and the slots are more than half as long as the given length.

In accordance with an added feature of the invention, the channels are wider below the surface of the housing than at the surface.

In accordance with an additional feature of the invention, at least one of the slots has a lower surface sloping downward toward the center of the housing.

In accordance with again another feature of the invention, the housing is formed of two housing halves each having one of the channels and one of the slots formed therein, and including a partition disposed between the housing halves.

In accordance with again a further feature of the invention, the partition has an upper knife-edge directly bordering and mutually separating the slots at the upper surface of the housing.

In accordance with again an added feature of the invention, the housing has two further channels and/or at least one additional channel formed therein for carrying a protective gas and cooling medium, respectively.

In accordance with again an additional feature of the invention, the upper surface of the housing has two further slots formed therein, each being in communication with a respective one of the further channels for carrying the protective gas to the upper surface of the housing, the first-mentioned slots carrying fuel and oxidant being disposed between the further slots.

In accordance with yet another feature of the invention, the further slots are substantially parallel to the first-mentioned slots.

In accordance with yet a further feature of the invention, the housing is formed of two housing halves each having one of the first-mentioned channels and first-mentioned slots formed therein and each having one of the further channels and further slots formed therein, and including a partition wall disposed between the housing halves.

In accordance with yet an added feature of the invention, the partition has an inverted V-shaped upper portion, as seen in cross section, and the knife-edge is formed by an upper edge of the upper portion.

In accordance with yet an additional feature of the invention, there is provided a separate third channel formed in the partition, and a third elongated slot formed in the upper surface of the partition and being in communication with the third channel.

In accordance with still another feature of the invention, there are provided means for delivering fuel and a sample to the third channel and means for delivering oxidant to the first and second channels, or vice versa.

In accordance with still an added feature of the invention, the third channel subdivides the partition into first and second partition parts, the first partition part having an upper knife-edge directly bordering and mutually separating the first and third slots at the upper surfaces of the housing halves, and the second partition part has an upper knife-edge directly bordering and mutually separating the second and third slots at the upper surfaces of the housing halves.

In accordance with a concomitant feature of the invention, the first and second channels are closer together in vicinity of the upper surfaces of the housing halves than below the upper surfaces.

Other features which are considered as characteristic for the invention are set forth in the appended claims.

Although the invention is illustrated and described herein as embodied in an atomic spectroscopy surface burner, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic perspective view of the atomic spectroscopy surface burner according to the invention;

FIG. 2 is a cross-sectional view of the burner of FIG. 1 showing the internal channels;

FIG. 3 is an enlarged, fragmentary view of the orifice portion of FIG. 2;

FIGS. 4 and 5 are views similar to FIG. 3 showing other embodiments of the orifice portion of the burner;

FIG. 6 is a perspective view of a spacer for widening the slots; and

FIG. 7 is a fragmentary perspective view of two of the spacers of FIG. 6 in the burner of FIG. 1.

Referring now to the figures of the drawing in detail and first particularly to FIG. 1 thereof, there is seen an atomic spectroscopy surface burner to be disposed between a radiation source and a monochromator, such as is illustrated on page 279 of the above-mentioned publication by Christian. The burner 1 has two housing halves 1a and 1b and a partition 2 disposed therebetween. Channels 3, 3', 4, 4' and 5 are machined in the metal, preferably titanium or stainless steel, housing halves.

As seen in FIG. 2, the channels 4, 4' are in communication with slots 6, 6', respectively, formed in the surface of the housing halves. On the other hand, the channels 3, 3' carry cooling medium and do not emerge to the surface. The channels are connected to non-illustrated supply tubes at the end faces of the housing halves shown in FIG. 1. The tubes supplying equivalent channels may lead from one source, so that, for instance, a single supply would be connected through tubes to the channels 3 and 3'. The opposite non-illustrated end faces of the housing halves may also have tubes connected to the channels.

FIG. 2 illustrates particularly clearly that the partition 2 is rectangular in vicinity of the end faces of the housing halves but has an inverted V-shaped or pointed cross-section in a central region within a slot 9, 9' formed in the housing halves 1a, 1b, respectively. An elongated knife-edge 2' is therefore formed along the top of the partition 2.

An additional channel 7 is formed in the housing half 1a. The channel 7 is in communication with a supply pipe 8 protruding downward from the housing half 1a. The channel 7 is widened toward the center of the housing 1, as shown in FIG. 2, in order to allow droplets to fall. The channel 7 has a sloping lower surface for this reason. The channels 7, 5 lead to the slots 9, 9', respectively.

Making reference to FIG. 3, it is clearly seen that the channels 5,7 widen toward the top thereof, because of surfaces 11, 12 forming the inverted V-shape of the partition 2. One of the channels 7, 5 carries fuel and the other carries oxidant. A sample or aerosol passes upward through the pipe 8 from a nebulizer and mixes with the fuel or oxidant in the channel 7. A one inch pipe fits most standard nebulizers. The mixture of nebulized sample and fuel or oxidant rises in the channel 7 to the slot 9 and the oxidant or fuel, whichever is not present in the channel 7, rises in the channel 5 to the slot 9', in the direction of the arrows. At the surface of the housing 1, the fuel is ignited and burns the sample, as they emerge from the slots.

The channels 4, 4' carry an inert gas such as argon which emerges from the slots 6, 6' and contains the flame above the slots 9, 9' in an argon sheath. This protects the flame from entrained air and is only needed to determine certain elements. As mentioned above, a cooling medium, such as water or gas, flows through the slots 3, 3' to cool the housing 1.

In the embodiment of FIG. 4, the same reference numerals are used as in FIGS. 1–3 for the same or similar elements. In FIG. 4 the partition 2 is subdivided into two partition parts 2a, 2b each having one of the surfaces 11, 12. The channels 5, 7 therefore have basically the same shape as in FIG. 3, although the length and angle of the surfaces 11, 12 may be varied to change the flow direction, rate of flow and shape of the flame. A further channel 10 is defined by the partition parts 2a, 2b. In this case, the channels 5, 7 carry the same substance, either fuel or oxidant, while the channel 10 carries which ever of the fuel and oxidant that are not carried in the channels 5, 7. The sample may be contained in the channel 10 or in the channels 5,7, by suitable placement of the supply pipe 8.

FIG. 5 shows an embodiment wherein the channels 5, 7 are offset toward each other as they approach the upper surface of the housing 1. This is accomplished by providing angled surfaces 13, 14 on the housing parts 1a, 1b, respectively. The surfaces 13, 14 are preferably, but not necessarily, parallel to the surfaces 11, 12, respectively. Again, by varying the angle and length of the surfaces 11–14 the shape of the flame as well as the direction and rate of flow in the channels, are regulated. It is also possible to vary the rate of flow in the channels by using individual valves in the tubes supplying the channels.

FIG. 6 shows a spacer 15 used to vary the width of the slots of the burner according to the invention. FIG. 7 illustrates two such spacers 15, 15', each being disposed on a respective side of the partition 2. The spacers widen the slots 9, 9' as shown in FIG. 7 by virtue of the fact that they move the housing halves 1a, 1b farther apart from each other. The U-shape of the spacers permits them to seal the outer edges of the partition to the housing halves with legs 15, 15b, and cross piece 15c, while having a wide open region at the slots 9, 9' and at the channels 5, 7.

FIG. 3 shows the spacers 15, 15' in phantom in the channels 5, 7.

FIG. 5 indicates that the spacers 15, 15' may be used when the channels 5, 7 are angled off and that spacers 16, 16' may be used to widen the channel 10. It must be understood that only the leg 15b of the spacers 15 is shown in FIGS. 3 and 5. The slots and channels are widened above the crosspiece 15c and between the legs 15a, 15b.

The slots 9, 9' provide a long path length for the flame. The length of the path is directly related to the amount of sample that will enter the flame and the concentration of free atoms which will be produced for absorbing source radiation for analysis. Therefore, the longer the path length, the better the analysis of the sample. The length of the slots 9, 9' are substantially 10 cm, and preferably more than half the length of the housing, in axial direction of the channels. The mere fact that a slot is provided instead of a hole or a series of holes, provides a continuous elongated, laminar flame, with a relatively simple and inexpensive construction. This is done while avoiding the disadvantages of premix burners, mentioned above. Other surface burners using holes, especially if capillary tubes are provided, are more difficult and thus expensive to construct. It is also impossible to vary the diameter of holes, whereas the slot width can be easily changed in the burner of the invention by using the spacers shown in FIGS. 6 and 7.

A list of fuels and oxidants which have been successfully used, is given below.

| Fuel | Oxidant |
| --- | --- |
| $H_2$ (hydrogen) | Air |
| $H_2$ | $O_2$ (oxygen) |
| $C_3H_8$ (propane) | $O_2$ |
| $C_2H_2$ (acetylene) and Air | $N_2O$ (nitrous oxide) |
| $C_2H_2$ and Air | $O_2$ |
| $C_2H_2$ and Ar (argon) | $O_2$ |

Samples of Cr (chromium), Al (aluminum), Cd (cadmium), Mg (magnesium) and Ca (calcium) have been analyzed.

I claim:

1. Atomic spectroscopy surface burner, comprising a housing having at least one channel for carrying fuel and at least one separate channel for carrying oxidant formed therein, said housing having an upper surface with two elongated slots formed therein, each of said slots being in communication with a respective one of said channels for delivering fuel and oxidant separately to said surface, and means for delivering a nebulized sample to said surface through one of said channels.

2. Burner according to claim 1, wherein said slots are elongated in axial direction of said channels.

3. Burner according to claim 1, wherein said housing has a given length in longitudinal direction of said slots, and said slots are more than half as long as said given length.

4. Burner according to claim 1, wherein said channels are wider below said surface of said housing than at said surface.

5. Burner according to claim 4, wherein at least one of said channels has a lower surface sloping downward toward the center of said housing.

6. Burner according to claim 1, wherein said housing at least one additional channel formed therein for carrying a cooling medium.

7. Burner according to claim 1, including means for widening said slots.

8. Atomic spectroscopy surface burner, comprising a housing having at least one channel for carrying fuel and at least one separate channel for carrying oxidant formed therein, said housing having an upper surface with two elongated slots formed therein, each of said slots being in communication with a respective one of said channels for delivering fuel and oxidant separately to said surface, means for delivering a nebulized sample to said surface through one of said channels, said housing being formed of two housing halves each having one of said channels and one of said slots formed therein, and including a partition disposed between said housing halves.

9. Burner according to claim 8, wherein said partition has an upper knife-edge directly bordering and mutually separating said slots at said upper surface of said housing.

10. Burner according to claim 9, wherein said partition has an inverted V-shaped upper portion, as seen in cross section, and said knife-edge is formed by an upper edge of said upper portion.

11. Burner according to claim 8, including spacers disposed adjacent said partition for widening said slots.

12. Atomic spectroscopy surface burner, comprising a housing having at least one channel for carrying fuel and at least one separate channel for carrying oxidant formed therein, said housing having an upper surface with two elongated slots formed therein, each of said slots being in communication with a respective one of said channels for delivering fuel and oxidant separately to said surface, means for delivering a nebulized sample to said surface through one of said channels, said housing having two further channels formed therein for carrying a protective gas, said upper surface of said housing having two further slots formed therein, each being in communication with a respective one of said further channels for carrying the protective gas to said upper surface of said housing, said first-mentioned slots carrying fuel and oxidant being disposed between said further slots, said housing being formed of two housing halves each having one of said first-mentioned channels and first-mentioned slots formed therein and each having one of said further channels and further slots formed therein, and including a partition wall disposed between said housing halves.

13. Burner according to claim 12, wherein said housing has at least one additional channel formed therein for carrying a cooling medium.

14. Burner according to claim 12, wherein said further slots are substantially parallel to said first mentioned slots.

15. Burner according to claim 12, wherein said partition has an upper knife-edge directly bordering and mutually separating said slots at said upper surface of said housing.

16. Burner according to claim 15, wherein said partition has an inverted V-shaped upper portion, as seen in cross section, and said knife-edge is formed by an upper edge of said upper portion.

17. Atomic Spectroscopy surface burner, comprising a housing formed of first and second housing halves each having an upper surface, a partition disposed between said housing halves and having an upper surface, a first channel formed in said first housing half, a first elongated slot formed in said upper surface of said first housing half and being in communication with said first channel, a separate second channel formed in said second housing half, a second elongated slot formed in said upper surface of said second housing half and being in communication with said second channel, a separate third channel formed in said partition, and a third elongated slot formed in said upper surface of said partition and being in communication with said third channel.

18. Burner according to claim 17, wherein said third channel subdivides said partition into first and second partition parts, said first partition part having an upper knife-edge directly bordering and mutually separating said first and third slots at said upper surfaces of said housing halves, and said second partition part has an upper knife-edge directly bordering and mutually separating said second and third slots at said upper surfaces of said housing halves.

19. Burner according to claim 17, wherein said first and second channels are closer together in vicinity of said upper surfaces of said housing halves than below said upper surfaces.

* * * * *